(12) United States Patent
Landis

(10) Patent No.: US 9,562,795 B2
(45) Date of Patent: Feb. 7, 2017

(54) DELUGE GUARD FOR GAS OR VAPOR DETECTION HEAD

(71) Applicant: Scott Technologies, Inc., Boca Raton, FL (US)

(72) Inventor: Jeffrey Lynn Landis, Waxhaw, NC (US)

(73) Assignee: Scott Technologies, Inc., Boca Raton, FL (US)

( * ) Notice: Subject to any disclaimer, the term of this patent is extended or adjusted under 35 U.S.C. 154(b) by 32 days.

(21) Appl. No.: 14/590,072

(22) Filed: Jan. 6, 2015

(65) Prior Publication Data

US 2015/0177029 A1 Jun. 25, 2015

Related U.S. Application Data

(63) Continuation of application No. PCT/US2013/049058, filed on Jul. 2, 2013.

(60) Provisional application No. 61/668,669, filed on Jul. 6, 2012.

(51) Int. Cl.
  *G01D 11/24* (2006.01)
  *G01N 27/02* (2006.01)
  *G01N 27/403* (2006.01)
  *G01N 33/00* (2006.01)

(52) U.S. Cl.
  CPC ......... *G01D 11/245* (2013.01); *G01N 33/0009* (2013.01); *Y10T 137/7043* (2015.04)

(58) Field of Classification Search
  CPC ............................ G01D 11/245; G01N 33/009
  USPC ......... 204/428; 73/19.12, 31.07, 431, 863.56
  See application file for complete search history.

(56) References Cited

U.S. PATENT DOCUMENTS 4,718,288 A * 1/1988 Leschonski .............. G01N 1/20
  141/34
5,018,395 A * 5/1991 Hickox ................... F04D 17/16
  73/23.2

* cited by examiner

*Primary Examiner* — Daniel S Larkin
(74) *Attorney, Agent, or Firm* — Christopher & Weisberg, P.A.

(57) ABSTRACT

A deluge guard has an impeller system for protecting a sensor head from liquid inundation.

5 Claims, 4 Drawing Sheets

DELUGE GUARD FOR GAS OR VAPOR DETECTION HEAD

CROSS-REFERENCE TO RELATED APPLICATION

This application is a continuation of International Application No. PCT/US2013/049058 filed Jul. 2, 2013, which claims the benefit of U.S. Provisional Patent Application No. 61/668,669 filed Jul. 6, 2012, the contents of which are incorporated herein by reference.

The present disclosure relates generally to devices and methods of protecting a sensor head from liquid saturation.

SUMMARY OF THE PRESENT INVENTION

The present application includes improvements in sensor head protection from liquid incursion.

BRIEF DESCRIPTION OF THE DRAWINGS

The accompanying drawings, which are incorporated herein and constitute part of this specification, illustrate exemplary embodiments of the invention, and together with the description above, serve to explain further features of the invention.

DETAILED DESCRIPTION OF THE PREFERRED EMBODIMENT

The invention includes improvements in shielding a sensor from liquid contact while allowing efficient passage of gas or vapor samples, e.g., combustible gas or vapor, to pass to the detector head sensor. The invention eliminates the need for creating a torturous open path to block liquid from getting to the sensor, removing the need for using stationary deflectors and baffles to prevent liquid penetration to the sensor in the detector head. As such response times to detect a gas are improved while improving performance during incidences of inundation of a sensor by a liquid and the resulting liquid saturation of the sensor.

Figure 1A:
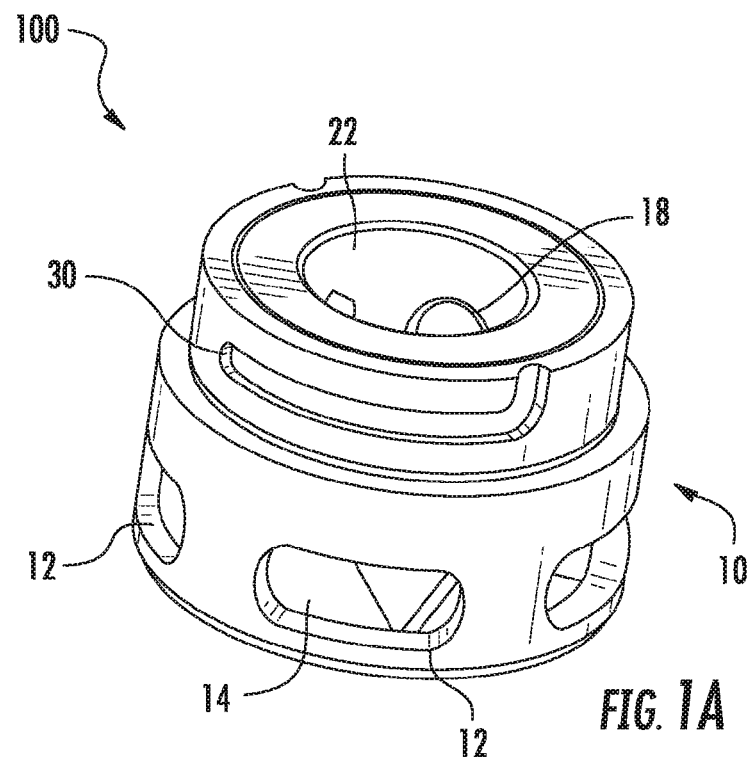
FIGS. 1A and 1B illustrate two prospective views of the sensor head protector of the invention.
Figure 1B:
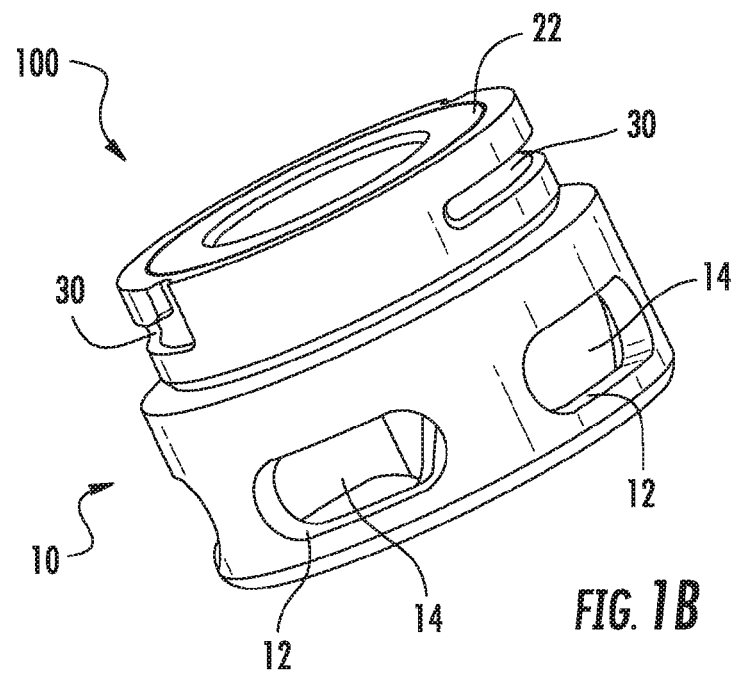
Figure 3:
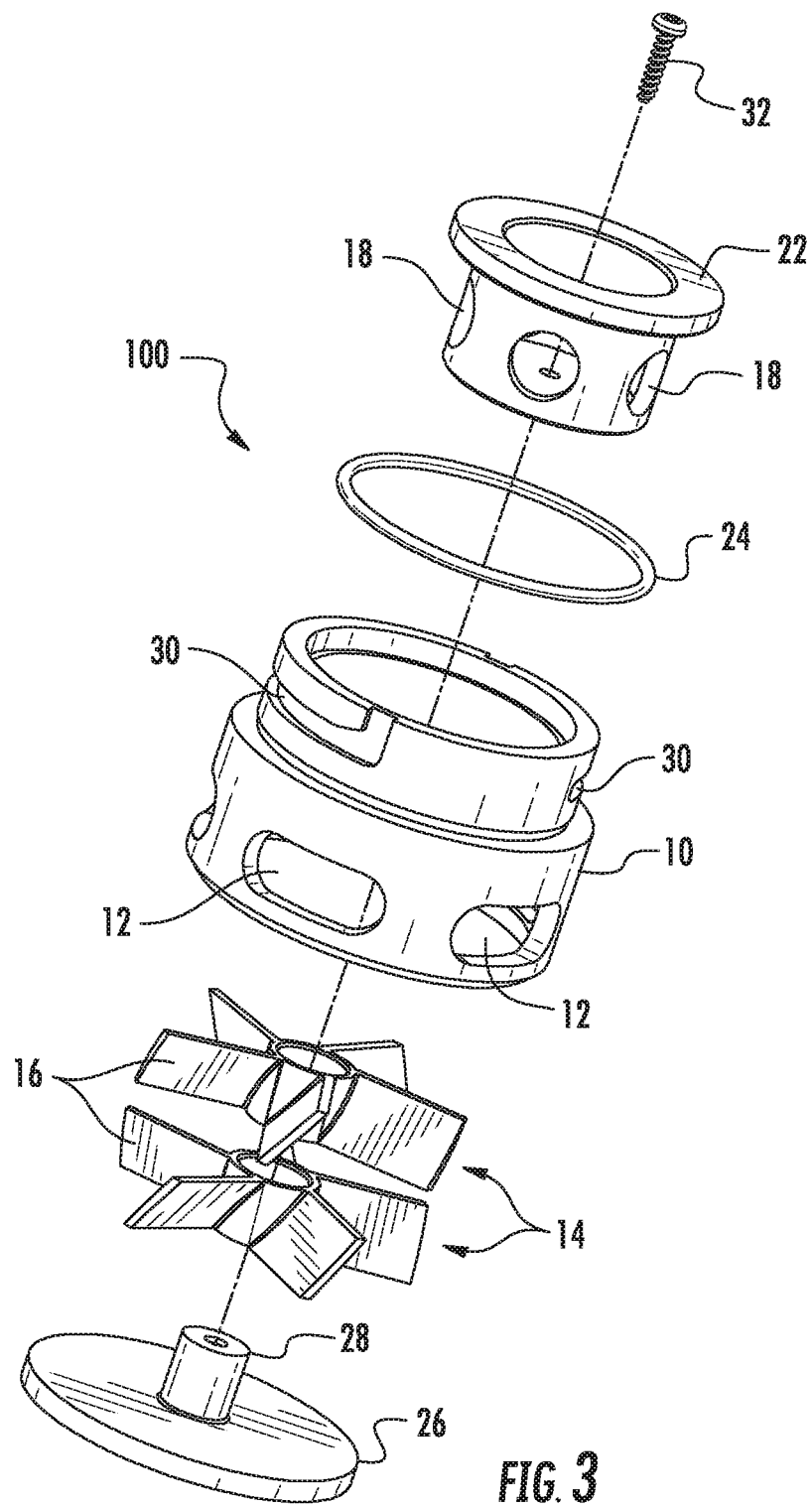
FIG. 3. illustrates an expanded side view of a second embodiment of the sensor head protector shown in FIGS. 1A and 1B.

As seen in FIGS. 1A and 1B, the invention comprises a deluge guard 100. In a preferred embodiment, the deluge guard 100 includes a deluge guard body 10 having one or more openings 12 along the circumference of the deluge guard body 10, generally in the lower section of the deluge guard body 10. An impeller deflector 14 with the ability to rotate is positioned within the deluge guard body 10. Although preferably a single impeller deflector 14 is positioned within the deluge guard body 10, multiple impeller deflectors 14 may be used either sequentially or in parallel within a single deluge guard body 10 (for example, as shown in FIG. 3). The impeller deflector 14 includes a blade system 16 configured to flow liquid to the other tips of the blades. As such, the blade system 16 generally includes multiple impeller deflector blades 16, preferably with the blades 16 having common angles of deflection, with the size, shape and angle of the impeller deflector blades 16 determinable by those skilled in the art of liquid deflection. The blade system 16 includes a plurality of blades radiating from the center point of the impeller deflector with the blades having an angle of tilt sufficient for communicating liquid to the outer edge of the blades 16 with the outer edge of the blades 16 being adjacent to the opening 12 within the deluge guard body 10. Representative angles of tilt from the axis of rotation of the impeller deflection blades 16 include, for example without limitation, from about 5 degrees to about 45 degrees, more preferably from about 10 degrees to about 40 degrees, still more preferably from about 10 degrees to about 35 degrees, and most preferably from about 10 degrees to about 30 degrees. The plurality of blades 16 may include any appropriate number of blades 16 for efficient transfer of liquid to the outer edges of the blades 16, with representative number of blades 16 being determinable by those skilled in the art, such as 4 blades or more, 5 to 10 blades, or 6 to 8 blades. Deluge guard baffle 22 with multiple holes 18 is positioned within the deluge guard body 10, adjacent to and above the impeller deflector 14. With the deluge guard baffle 22 being placed above the impeller deflector 14, the openings formed in each section do not radially align. Thus , the deluge guard body 10 provides a protective enclosure between the deluge guard baffle 22 and the deluge guard cap 26. Also shown are mounting slots 30 on opposite sides of the deluge guard body 10 for mounting the deluge guard 100 adjacent to a sensor head 200 (shown in FIG. 4).These deluge guard mounting slots 30 provide quarter-turn mounting to pins inside the detector head cap. Although slots 30 are shown, any appropriate mounting or attaching mechanism 30 may be used, with such mounting or attaching mechanism 30 determinable by those skilled in the art of sensor head mounting.

Compositions of the deluge guard 100 include any appropriately resilient materials suitable in toxic/hazardous environments and capable of withstanding liquid saturation during its normal course of operation. Representative compositions include, for example without limitation, non-corrosive metals, such as stainless steel, plastics and other like polymers resistant to corrosion or other types of degradation from water, or acidic and/or basics compounds, such as $H_2S$, CO, $SO_2$, phosphines, phosgenes, nitrous gas, etc. Sizes of the deluge guard 100 include any appropriate dimensions suitable for a given sensor head 200, with representative sizes including circumferences of from about two inches to about ten inches, and heights for from about one inch to about five inches.

Figure 2:
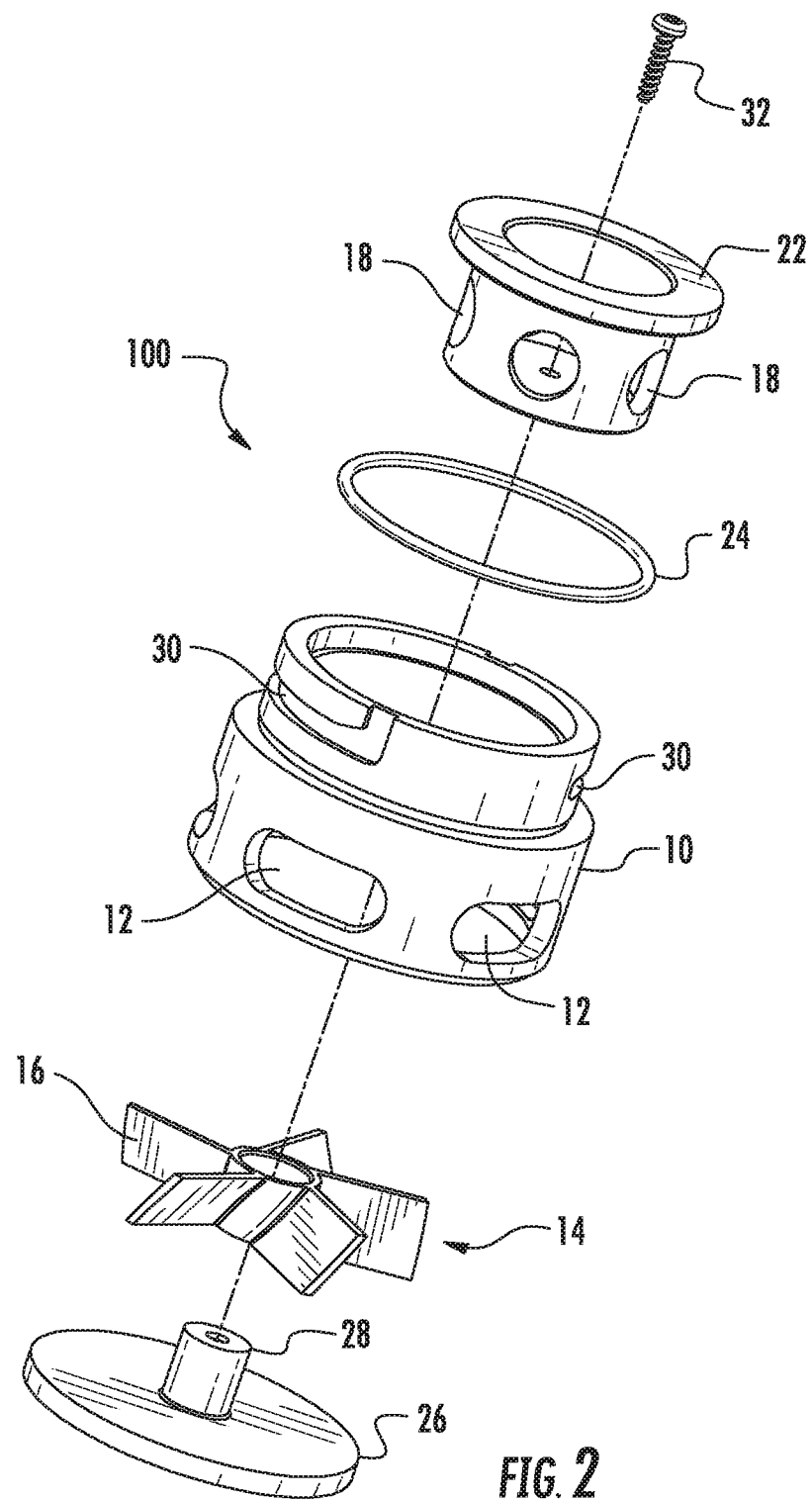
FIG. 2 illustrates an expanded side view of a first embodiment of the sensor head protector shown in FIGS. 1A and 1B.

FIGS. 2 and 3 are illustrations showing expanded views of the preferred embodiments of the deluge guard 100. The deluge guard 100 is constructed by inserting the deluge guard baffle 22 within the circumference of the deluge guard body 10. The baffle 22 provides a shield and directs any splashing liquid away from the sensor. The deluge guard body 10 provides a mounting to a detector head cap and has slots or openings 12 for gas and liquid discharge while providing a protective enclosure between the baffle 22 and end cap. The holes 18 along the circumference of the baffle 22 reside within the guard body 10 and are located above the guard body openings 12. An impeller deflector 14 is inserted into the opposite end of the guard body 10 having its impeller blades 16 in a planar position adjacent to the openings 12 of the guard body 10. The impeller deflector 14 directs diffused gas and vapor up through baffle openings 18 to a sensor behind the detector head cap and rotates when sprayed with liquid and forces water out through the slots 12 in the deluge guard body 10. When positioned within the guard body 10 the impeller blades 16 of the impeller deflector 14 are clear of obstructions from the interior of the guard body 10 as to permit unimpeded movement about is center. A deluge guard cap 26 having a stem 28 is used to secure the components of the deluge guard 100 together while the stem 28 allows an axis of rotation for the free moving impeller deflector 14. The deluge guard gap 26 provides a pivot for the impeller deflector 14 and protection from liquid directed against the bottom of the deluge guard 100 assembly, while providing an anchor for the assembly screw 32 which holds the deluge guard 100 together. The screw, or other appropriate fastening device, 32 secures the base of the guard baffle 22 to the cap 26.

Figure 4:
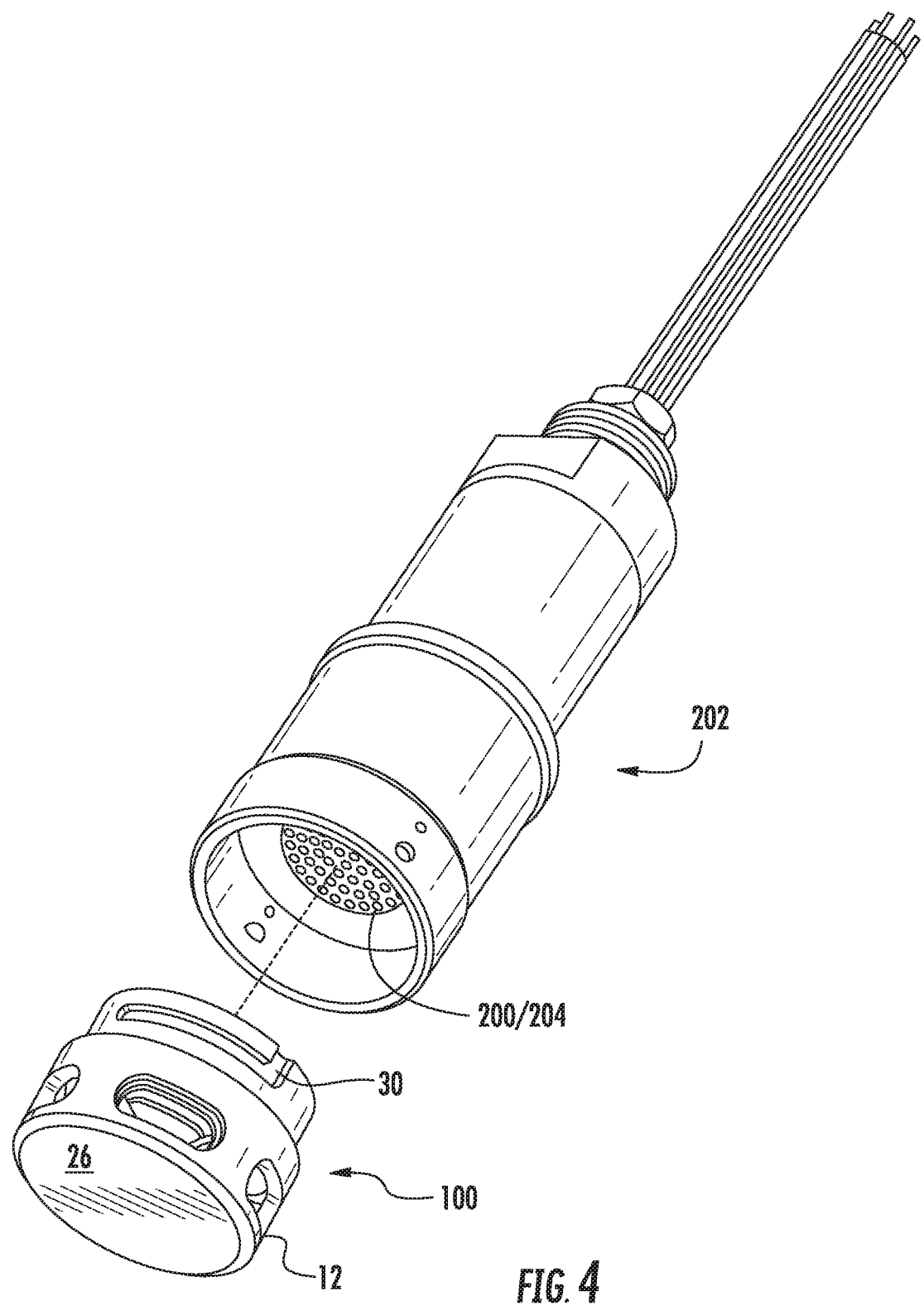
FIG. 4 illustrates the sensor head protector of FIGS. 1A and 1B combined with a sensor head.

Referring to FIG. 4, the deluge guard 100 attaches to a detector head assembly 202 using a twisting motion to engage the mounting slots 30 (shown in FIGS. 2 and 3 as quarter turn slots) to the detector head assembly 202. An O-ring 24 (shown in FIGS. 2 and 3), located along the upper edge of the mid-section of the guard body 10, and below the mounting slots 30, seals the deluge guard to the face of the detector head cap and provides an air-tight seal for an area encompassing a detector head sensor 200 of the detector head assembly 202. A detector head cap screen 204 is located in front of the detector head sensor 200. In operation, the deluge guard 100 is assembled and attached to the detector head assembly 202. Once subjected to moving liquid forces, e.g., a liquid stream, the impeller deflector 14 freely rotates from forces exerted against the blade system 16 by the flow of liquid, causing the angled impeller deflector blades 16 to pass the liquid stream out through openings 12 within the deluge guard body 10, and preventing the liquid from filling the inside of the deluge guard body 10. As such, liquid is prevented from being forced up through the deluge guard baffle holes 18 and detector cap screen 204, protecting the detector head sensor 200 from becoming disabled or damaged by the liquid. When liquid forces are absent, the impeller deflector 14 remains stationary, and when stationary, the series of angled blades within the blade system 16 direct diffused gas or vapor up through the deluge guard baffle holes 18 to the detector head sensor 200 retained behind the screen of the detector head cap screen 204.

In a preferred embodiment, this deluge guard 100 provides a wash-down (e.g., cleaning an area around the sensor by flushing with water without de-energizing the sensor) capability without affecting the response time of the sensor. Preferably the response time of the sensor with the invention is from about ten seconds or less.

In another embodiment, movement of the impeller deflector 14 may be caused by a motor or other force imparting device to aid in the expulsion of the liquid from the deluge guard body 10.

The size and shape of the baffle holes 18 may be designed to specifically aid in response time, e.g., circular, diamond, oval, elongated, etc., with the appropriate selection being determinable by one skilled in the art of sensor performance.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A deluge guard for protecting a sensor head from inundation by liquid, comprising:
    a deluge guard body, the deluge guard body having at least one opening along the circumference of the deluge guard body;
    an impeller deflector rotationally positioned within the deluge guard body;
    a blade system within the impeller deflector, the blade system having a plurality of blades radiating from a center point of the impeller deflector, the blades having an angle of tilt sufficient for communicating liquid to the outer edges of the blades, the outer edges of the blades being adjacent to the openings within the deluge guard body; and,
    a deluge guard baffle, the baffle forming openings therein, positioned within the inner circumference of the deluge guard body and above the impeller deflector.

2. The deluge guard of claim 1, wherein a plurality of impeller deflectors are positioned within the deluge guard body.

3. The deluge guard of claim 1, wherein the plurality of blades is from about 6 blades to about 8 blades.

4. The deluge guard of claim 1, wherein the angle of tilt of the blades is from about 10 degrees to about 30 degrees.

5. The deluge guard of claim 1, wherein the deluge guard body has a plastic composition.

* * * * *